(12) United States Patent
Petrali

(10) Patent No.: US 6,637,885 B2
(45) Date of Patent: Oct. 28, 2003

(54) METHOD FOR SELF-DETECTION OF PUPILLARY RESPONSE

(75) Inventor: John P. Petrali, Churchville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 12 days.

(21) Appl. No.: 10/101,966

(22) Filed: Mar. 21, 2002

(65) Prior Publication Data

US 2002/0135737 A1 Sep. 26, 2002

Related U.S. Application Data

(60) Provisional application No. 60/278,615, filed on Mar. 26, 2001.

(51) Int. Cl.[7] .................................................. A61B 3/02
(52) U.S. Cl. ....................................................... 351/223
(58) Field of Search ............................... 351/205, 202, 351/221, 222, 223, 246, 247; 600/558; 222/383.1; 604/300, 301, 327, 289, 294, 297

(56) References Cited

U.S. PATENT DOCUMENTS

| | | | | | |
|---|---|---|---|---|---|
| 5,171,307 | A | * | 12/1992 | Sanning | 604/327 |
| 5,387,202 | A | * | 2/1995 | Baron | 604/300 |
| 5,588,564 | A | * | 12/1996 | Hutson et al. | 222/383.1 |
| 5,892,568 | A | * | 4/1999 | Carter | 351/205 |

* cited by examiner

*Primary Examiner*—George Manuel
(74) *Attorney, Agent, or Firm*—Elizabeth Arwine

(57) ABSTRACT

A method for self-detection of exposure to organophosphates includes (a) providing a device for monitoring pupillary response; (b) switching the device on and placing the eyeglass cup over the eye to be tested; (c) blocking light from entering the other eye; and (d) observing whether or not the pupil in the eye to be tested dilates. The device for monitoring pupillary response includes a housing; an eyeglass cup attached to the housing, the eyeglass cup including an insert tower and a glass aperture disposed on an end of the insert tower; a power supply disposed in the housing; a light source connected to the power supply; and a switch for controlling power to the light source.

3 Claims, 3 Drawing Sheets

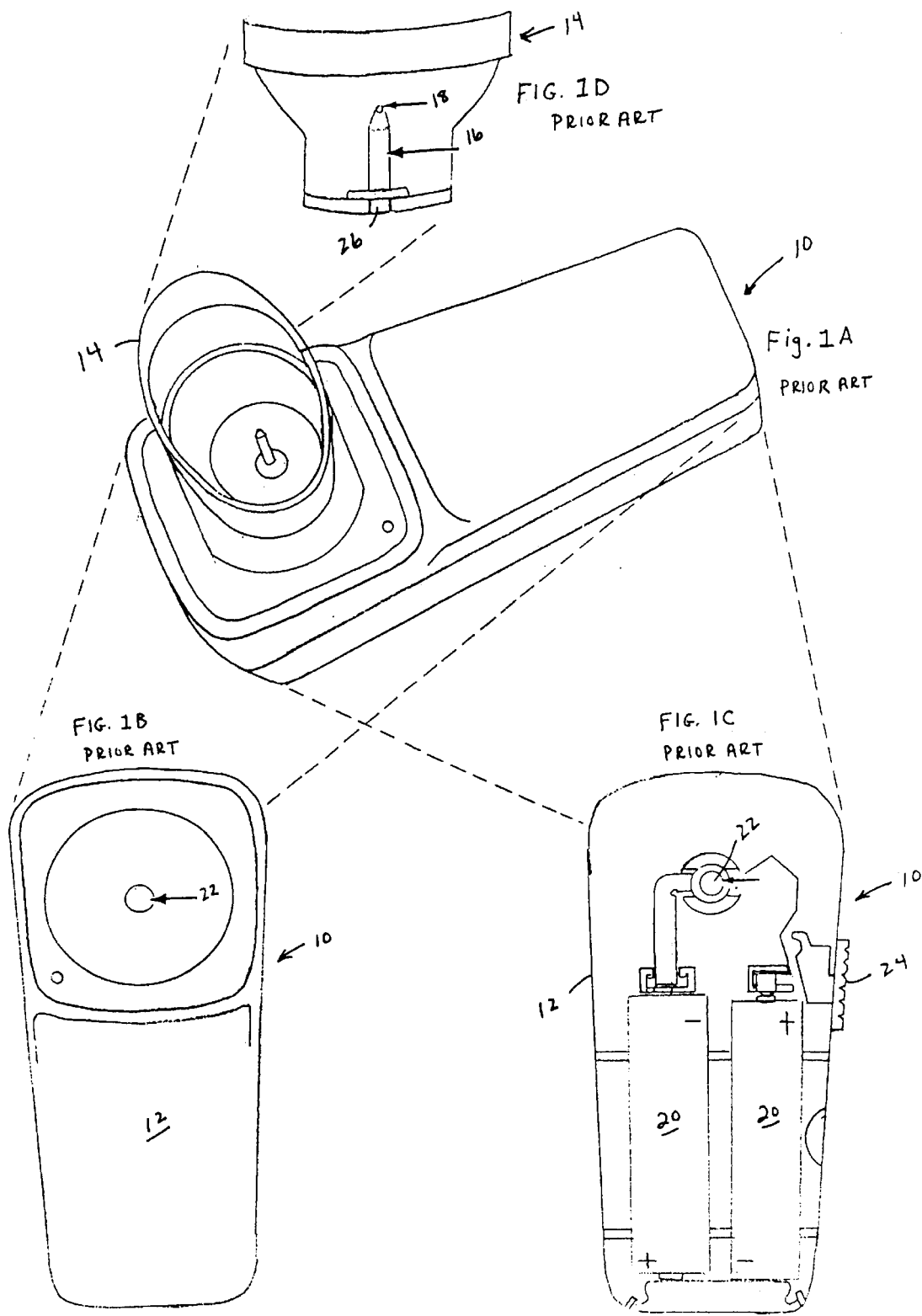

METHOD FOR SELF-DETECTION OF PUPILLARY RESPONSE

RELATED APPLICATIONS

This application claims the benefit of priority from U.S. provisional patent application serial No. 60/278,615 filed Mar. 26, 2001, which is hereby incorporated by reference.

STATEMENT OF GOVERNMENT INTEREST

The invention described herein may be manufactured and used by or for the Government of the United States of America for government purposes without the payment of any royalties therefor.

BACKGROUND OF THE INVENTION

The present invention relates in general to methods for monitoring pupillary response and in particular to a method for self-detection of pupillary response.

Human beings may be exposed to organophosphates in a variety of ways. Organophosphates are found in "nerve gas" and some pesticides. Thus, humans may be exposed to organophosphates in a military situation, in a terrorist attack, in a laboratory or in an agricultural setting. To minimize harm from organophosphates, it is important to seek treatment as quickly as possible after exposure.

One of the first symptoms of exposure to organophosphates is miosis. Miosis is constriction of the pupil of the eye, or "fixed" pupil. Miosis may be temporary or long standing. After exposure to organophosphates, miosis begins within seconds and may last for hours, weeks or even months. Miosis results in dim vision, blurred vision, inadequacies of depth perception and diminished visual acuity. In the case of induced miosis, the affected pupil will not respond to consensual inputs.

There is a need for a method of quickly determining whether a human being may have been exposed to organophosphates. If it appears that an individual may have been exposed, then appropriate medical treatment can be pursued immediately.

An object of the present invention is to provide a method of determining if a human may have been exposed to organophosphates. The method allows for self-detection. Thus, another person is not necessary to implement the method. The feature of self-detection is important because another individual is not always present in situations involving exposure to organophosphates. The method uses a small, portable ocular device about the size of a king-size pack of cigarettes. Therefore, the device may be easily carried to any location, however remote.

Further objects, features and advantages of the invention will become apparent from the following detailed description taken in conjunction with the following drawing.

BRIEF DESCRIPTION OF THE DRAWINGS

Throughout the Figures, reference numerals that are the same refer to the same features.

FIG. 1A is a perspective view of a prior art ocular device.

FIG. 1B is a top view of the device of FIG. 1A with the eyeglass cup removed.

FIG. 1C is a cutaway view of the device of FIG. 1A.

FIG. 1D is a cutaway view of an eyeglass cup used with the device of FIG. 1A.

DETAILED DESCRIPTION OF THE PREFERRED EMBODIMENTS

Figure 2B:
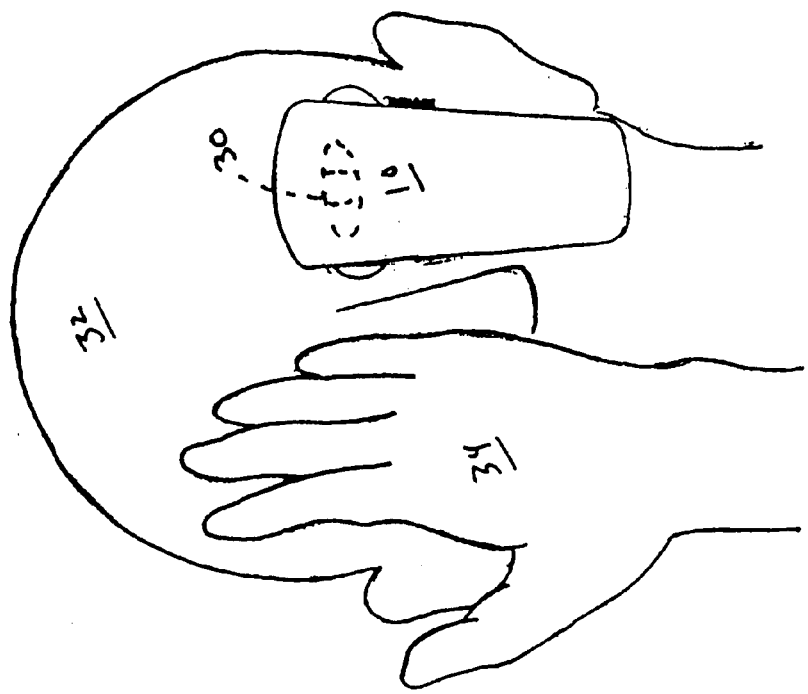
FIG. 2B is a front view of FIG. 2A.

An ocular device 10 used with the method of the present invention is shown in FIGS. 1A–1D. The device 10 was designed in the early 1980's for use by contact lens wearers to detect contaminants on the surface of their hard contact lenses. At that time, contaminants were a serious problem for persons wearing the then state-of-the-art hard contact corneal lenses. Early self-detection, identification and removal of contaminants were obligatory to avoid the corneal irritation, edema, and conjunctivitis that accompanied the wearing of "dirty" lenses. The process of removing contaminants consisted of progressive wash steps. The device 10 was used to monitor the progress and effectiveness of the removal process.

FIG. 1A is a perspective view of the prior art ocular device 10. Device 10 includes a housing 12 and an eyeglass cup 14 attached to the housing 12. Housing 12 may be made of, for example, plastic. Eyeglass cup 14 may be attached to housing 12 by an interference fit or threads or may be formed integrally with housing 12. FIG. 1B is a top view of the device 10 of FIG. 1A with the eyeglass cup 14 removed.

FIG. 1C is a cutaway view of the device 10 of FIG. 1A showing the interior of housing 12. The interior of housing 12 includes a power supply 20 that may be, for example, two size A batteries. Power supply 20 is connected to light source 22 through switch 24. Light source 22 can be an ordinary flashlight bulb, such as a Philips 222. Switch 24 is operable to connect and disconnect power to light source 22.

FIG. 1D is a cutaway view of an eyeglass cup 14 used with the device 10 of FIG. 1A. The eyeglass cup 14 includes an insert tower 16 and a glass aperture 18 disposed on an end of the insert tower 14. Portion 26 of the eyeglass cup 14 is transparent to allow light to pass from light source 22 to insert tower 16. The remainder of eyeglass cup 14 is opaque and may be made of, for example, plastic. Insert tower 16 may be made of, for example, metal. The end of insert tower 16 forms a cone. The glass aperture 18 is disposed at the tip of the cone. Glass aperture 18 may be made of, for example, sintered glass or fiber optic glass.

The device 10 is placed with the eyeglass cup 14 surrounding one eye. The switch 24 is turned on and the light source 22 provides illumination to the glass aperture 18. By observing the glass aperture 18, the user sees an image of his or her pupil. As described in more detail below, it is the change, or lack thereof, in the size of the pupil that determines whether or not the user may have miosis.

Figure 2A:
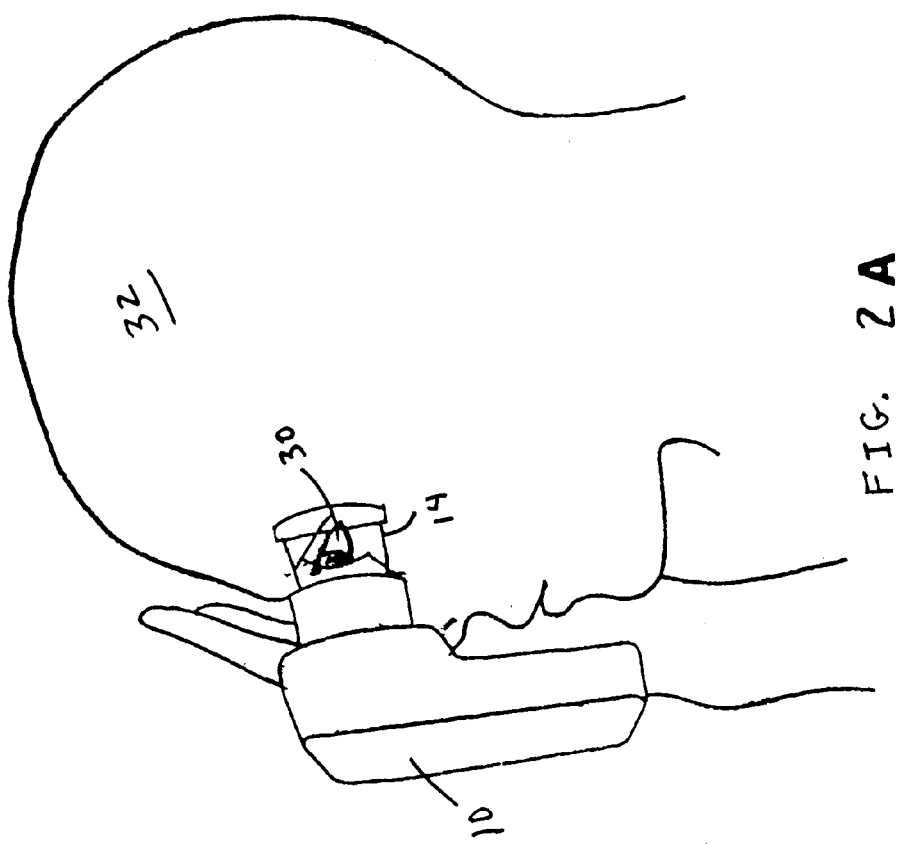
FIG. 2A is a side view showing the method of the invention.

FIG. 2A is a side view showing the method of the invention. FIG. 2B is a front view of FIG. 2A. FIGS. 2A and 2B show a human 32 using the ocular device 10. In FIG. 2A, for illustration purposes only, the eyeglass cup 14 appears transparent so that one may view the eyeball 30. However, as discussed above, the eyeglass cup 14 is actually opaque.

The method for self-detection of exposure to organophosphates includes the steps of switching the device 10 "on" and placing the eyeglass cup 14 over the eye 30 to be tested. The other eye is blocked to keep light from entering. Blocking can be accomplished using the hand 34 of the user 32. Because light is blocked, the pupil of the eye covered with the hand will normally dilate. When the pupil of the eye covered with the hand dilates, the pupil of the eye 30 being tested should respond consensually, i.e., the pupil of the eye 30 being tested should also dilate. The user 32 observes whether or not the pupil of the eye 30 dilates by viewing the image of the pupil on the glass aperture 18 (FIG. 1D). If the pupil of the eye 30 does not dilate, then it is possible that miosis has occurred.

Figure 3:
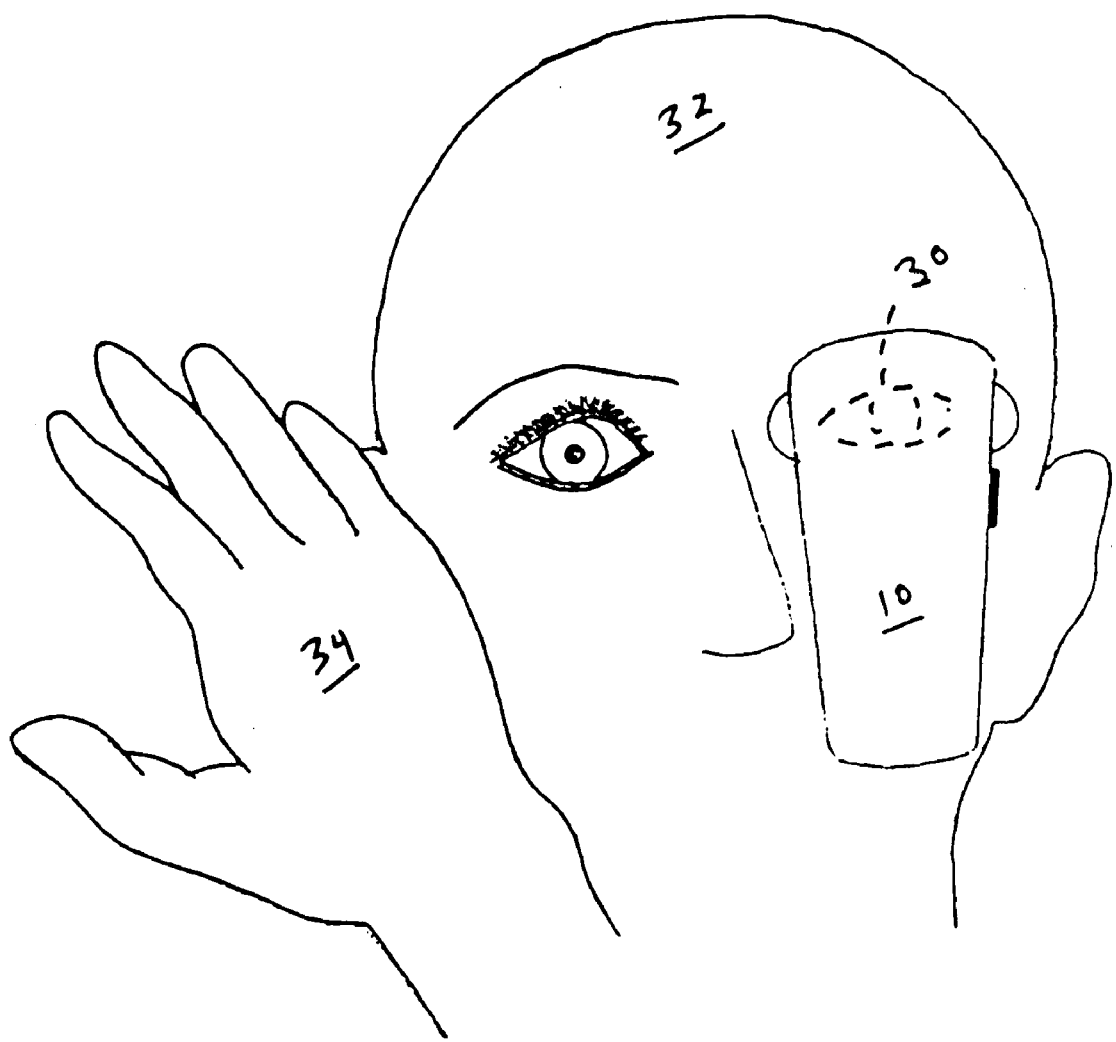
FIG. 3 is a front view showing the method of the invention.

As shown in FIG. 3, to further test eye 30, the user 32 removes his hand from the blocked eye thereby allowing light to enter the now unblocked eye. As light enters the unblocked eye, the pupil of the unblocked eye should restrict. As a consensual response, the pupil of the eye 30 being tested should also restrict. The user 32 observes whether or not the pupil of the eye 30 restricts by viewing the image of the pupil on the glass aperture 18. If the pupil of the eye 30 does not restrict, then it is possible that miosis has occurred. The respective roles of the user's eyes may be reversed and the other eye also tested in the manner described above.

Light which is being transmitted through the aperture 18 of the tower 16 is transmitted along the optical axis (center) of the eye 30 and is recorded on the retina. Along the axis of the eye is the cornea, the crystalline lens and the iris. The iris surrounds the lens and controls the size of the pupil. As light is transmitted, the subject (person) actually sees the image of the crystalline lens which is recorded on the retina. Therefore, any changes in the optical axis pathway which would interfere with the transmittance of light through the crystalline lens, including any changes in the diameter of the pupil (iris dynamics), are detectable.

While the invention has been described with reference to certain preferred embodiments, numerous changes, alterations and modifications to the described embodiments are possible without departing from the spirit and scope of the invention, as defined in the appended claims and equivalents thereof.

What is claimed is:

1. A method for self-detection of exposure to organophosphates, comprising:
   (a) providing a device for monitoring pupillary response, the device including
       a housing;
       an eyeglass cup attached to the housing, the eyeglass cup including an insert tower and a glass aperture disposed on an end of the insert tower;
       a power supply disposed in the housing;
       a light source connected to the power supply; and
       a switch for controlling power to the light source;
   (b) switching the device on and placing the eyeglass cup over the eye to be tested;
   (c) blocking light from entering the other eye; and
   (d) observing whether or not the pupil in the eye to be tested dilates.

2. The method of claim 1 further comprising
   (e) unblocking the eye that was blocked in step (c) thereby allowing light to enter; and
   (f) observing whether or not the pupil in the eye to be tested restricts.

3. The method of claim 2 further comprising placing the eyeglass cup over the eye not tested and repeating steps (c) through (f).

* * * * *